US007244416B2

United States Patent
Meyer et al.

(10) Patent No.: US 7,244,416 B2
(45) Date of Patent: Jul. 17, 2007

(54) STABILIZED PHOTOPROTECTIVE COMPOSITION

(75) Inventors: Thomas A. Meyer, Germantown, TN (US); Donathan G. Beasley, Memphis, TN (US)

(73) Assignee: Schering-Plough Healthcare Products, Inc., Memphis, TN (US)

( * ) Notice: Subject to any disclaimer, the term of this patent is extended or adjusted under 35 U.S.C. 154(b) by 325 days.

(21) Appl. No.: 10/645,253

(22) Filed: Aug. 21, 2003

(65) Prior Publication Data

US 2004/0081629 A1 Apr. 29, 2004

Related U.S. Application Data

(60) Provisional application No. 60/405,404, filed on Aug. 22, 2002.

(51) Int. Cl.
| | |
|---|---|
| *A61Q 17/00* | (2006.01) |
| *A61Q 17/04* | (2006.01) |
| *A61Q 19/00* | (2006.01) |
| *A61K 8/00* | (2006.01) |
| *A61K 8/04* | (2006.01) |
| *A61K 8/02* | (2006.01) |

(52) U.S. Cl. .................. 424/59; 424/60; 424/400; 424/401

(58) Field of Classification Search .................. 424/59, 424/60, 400, 401
See application file for complete search history.

(56) References Cited

U.S. PATENT DOCUMENTS

| | | | |
|---|---|---|---|
| 4,387,089 A | 6/1983 | De Polo | 424/59 |
| 5,576,354 A | 11/1996 | Deflandre et al. | 514/685 |
| 5,587,150 A | 12/1996 | Deflandre et al. | 424/59 |
| 5,827,508 A | 10/1998 | Tanner et al. | 424/59 |
| 5,849,273 A | 12/1998 | Bonda et al. | 424/59 |
| 5,985,251 A | 11/1999 | Gonzenbach et al. | 424/59 |
| 5,989,528 A | 11/1999 | Tanner et al. | 424/59 |
| 6,033,649 A | 3/2000 | Gonzenbach et al. | 424/60 |
| 6,071,501 A | 6/2000 | Robinson | 424/59 |
| 6,090,369 A | 7/2000 | Stewart | 424/59 |
| 6,444,195 B1 * | 9/2002 | Cole et al. | 424/60 |

OTHER PUBLICATIONS

Letter dated Jun. 19, 2006 from John O'Mullana, B.Sc, Ph.D., Group VP R&D for Consumer Health Care In Schering-Plough to Division of Dockets Management In the Food and Drug Administration, pp. 1-12.
Cole, Curtis, "Multicenter evaluation of sunscreen UVA protectiveness with the protection factor test method", Journal of the American Academy & Dermatology, vol. 30, No. 5, Part 1, pp. 729-736.
Editor, Urbach, Frederick, "Biological Responses to Ultraviolet A Radiation", Valdenmar Publishing Company, Overland Park, Kansas, pp. 335-345.

* cited by examiner

*Primary Examiner*—Shelley A. Dodson
(74) *Attorney, Agent, or Firm*—Matthew J. Golden

(57) ABSTRACT

Sunscreen compositions contain the active ingredients avobenzone, zinc oxide and phenylbenzimidazole sulfonic acid. The phenylbenzimidazole sulfonic acid protects avobenzone against photodegradation.

14 Claims, No Drawings

STABILIZED PHOTOPROTECTIVE COMPOSITION

INTRODUCTION TO THE INVENTION

The present invention relates to compositions for skin application to protect against the harmful effects of ultraviolet radiation, particularly the effects of solar radiation.

It is now generally accepted that ultraviolet radiation can be a serious health hazard. Even a limited exposure to the sun's rays which is incidental to daily life activities is known to cause chronic skin damage, including conditions such as skin aging, keratotic lesions and malignant cellular changes. Those who spend a very large amount of time in the outdoors, such as from career or recreational pursuits, have a greatly enhanced risk of developing such conditions, as well as suffering from acute adverse effects such as sunburn (erythema). Fortunately, numerous sunscreening products are commercially available at reasonable cost, for application to the skin as a protection against exposure to solar ultraviolet radiation.

Sunscreening compositions take a number of forms, including lotions and creams, sticks, sprays and others. Their activity results from inclusion of one or more ultraviolet-absorbing or -scattering active ingredients, selected from lists of such ingredients that have been approved by governmental regulatory agencies in the various countries where the products are to be marketed. In the United States, sunscreening products are classified as nonprescription drugs and their approved active ingredients are listed in Title 21, Code of Federal Regulations, Part 352.

The ultraviolet components of solar radiation which are known to cause skin damage include radiation having wavelengths in the range of 290–320 nanometers and generally referred to as "UV-B," as well as radiation having wavelengths in the range of 320–400 nanometers and generally referred to as "UV-A." "UV-C" radiation, having wavelengths in the range of 200–290 nanometers, is filtered out of solar radiation by the atmospheric ozone layer, so is not considered to be a serious threat in most of the world. Only UV-B radiation was initially considered to be of great importance, so historically the majority of approved sunscreen active ingredients are active in this range of wavelengths. However, the more recently developed products are formulated to absorb and/or scatter wavelengths in both UV-B and UV-A regions of the ultraviolet radiation spectrum. A very popular ingredient which absorbs in the UV-A range is known as "avobenzone" and has the INCI name Butyl methoxydibenzoylmethane; this substance is sold by Roche Vitamins Inc. of Parsippany, N.J. U.S.A. under the trademark PARSOL 1789. Since a particular organic molecule will exhibit its strongest absorption at a point within a range of wavelengths, and may not be very effective at some other points within that range, it is a very common practice to utilize a combination of ingredients in a product so that effective absorption over the majority of harmful wavelengths will be obtained.

Although the typical sunscreening product uses one or more organic chemical active ingredients to absorb ultraviolet radiation, inorganic particulate physical sunblocking ingredients such as titanium dioxide and zinc oxide are becoming of increasing importance. These agents can provide a broad spectrum of protection, since the particles absorb, reflect and/or scatter radiation in a rather indiscriminate manner. By reducing the particle sizes to very small values, such as below about 400 nanometers, large amounts of particulate ingredients can be incorporated into a product without affecting the natural skin coloration when the product is applied. In addition, it has been discovered that product characteristics can be improved by providing the particles with coatings to modify the affinity for either water or water-insoluble formulation components. Products containing combinations of organic and particulate inorganic active ingredients, to provide protection against the full wavelength range of harmful ultraviolet radiation, have become common.

Avobenzone is known to lack chemical stability in sunscreen products, and also exhibits a lack of photostability during prolonged exposure to ultraviolet radiation. However, since it is a very desirable component of many sunscreening products, considerable effort has been devoted to studies of these instabilities. Combinations of some other sunscreening active agents with avobenzone have been reported to decrease the photostability of avobenzone, while combinations with certain other ingredients are reported to enhance avobenzone photostability. U.S. Pat. Nos. 5,576,354 and 5,587,150 to Deflandre et al. describe the photostabilization of avobenzone in sunscreen compositions by adding a diphenylacrylate sunscreen ingredient, such as octocrylene, in molar ratios of diphenylacrylate to avobenzone at least 0.8. U.S. Pat. No. 5,827,508 to Tanner et al. reports that avobenzone can be made to have improved chemical stability and photostability in a sunscreen product formulation by incorporation of surface-treated zinc oxide particles, silicone-treated zinc oxide being particularly useful for this purpose. U.S. Pat. No. 5,985,251 to Gonzenbach et al. teaches that stable sunscreen compositions can be prepared to contain avobenzone, a diphenylacrylate or benzylidene camphor derivative and a water-soluble p-methoxycinnamate. U.S. Pat. No. 5,989,528 to Tanner et al. reports that avobenzone can be made more stable by including in its formulations a diphenylacrylate derivative, when the molar ratio of diphenylacrylate to avobenzone is less than 0.8. U.S. Pat. No. 6,071,501 to Robinson states that combinations of dibenzoylmethane derivatives and octyl p-methoxycinnamate are not photostable, unless the molar ratio of the methoxycinnamate to the dibenzoylmethane is in the range of 0.15:1 to 1:1. U.S. Pat. No. 6,090,369 to Stewart proposes a stable sunscreen composition that contains avobenzone, octyl methoxycinnamate and either titanium dioxide or zinc oxide; octocrylene is an optional component.

Prolonged protection against the UV-A radiation is very important, as evidenced by the numerous approaches that have been taken to improve avobenzone photostability. It is always desired to improve the performance characteristics of sunscreening products, and the present invention provides a further improvement over the current state of the art.

SUMMARY OF THE INVENTION

The invention includes a stable photoprotective composition containing the active ingredients avobenzone, zinc oxide and phenylbenzimidazole sulfonic acid. The phenylbenzimidazole sulfonic acid component provides ultraviolet-absorbing properties and acts to stabilize avobenzone against photodegradation. In general, the avobenzone will be present in amounts about 1 to about 3 weight percent, the zinc oxide will be present in amounts about 1 to about 25 weight percent and the phenylbenzimidazole sulfonic acid will be present in amounts about 0.5 to about 4 weight percent. When the photoprotective composition is in the form of an emulsion, other components will include water and an emulsifier.

DETAILED DESCRIPTION

In this document, chemical substances are wherever possible identified by either their chemical names or by adopted names taken from J. A. Wenninger et al., Eds., *International Cosmetic Ingredient Dictionary and Handbook*, 8$^{th}$ Ed., The Cosmetic, Toiletry, and Fragrance Association, Washington, D.C., 1999. Percentages are intended to mean "weight percent," unless the context clearly indicates otherwise.

Sunscreening compositions generally are permitted to contain only the active ingredients that have been approved by governmental authorities, and frequently those authorities also specify the amounts of each approved ingredient that are permitted to be present in a product. The following active ingredients are currently listed in Title 21, Code of Federal Regulations, Section 352.10 as being approved for inclusion in products sold in the United States as non-prescription sunscreen drugs: aminobenzoic acid; avobenzone; cinoxate; dioxybenzone; homosalate; menthyl anthranilate; octocrylene; octyl methoxycinnamate; octyl salicylate; oxybenzone; Padimate O; phenylbenzimidazole sulfonic acid; sulisobenzone; titanium dioxide; trolamine salicylate; and zinc oxide. Section 352.20 of the same Title 21 describes the permitted combinations of ingredients; in general, each active ingredient in a permitted combination is required to be present in at least a sufficient amount to contribute an SPF value of 2, so an amount making this contribution is considered herein to be the minimum "sunscreening-effective" concentration of an active ingredient. The regulations prescribe maximum concentrations of 3 percent avobenzone, 25 percent zinc oxide and 4 percent phenylbenzimidazole sulfonic acid in a sunscreening product. Some countries allow the use of other active ingredients and these are also suitable for inclusion as components of the compositions of this invention, where their use is legally permitted; in addition, the permitted concentrations of active ingredients vary somewhat by country.

Beginning in September 2002, the official adopted name in the United States for menthyl anthranilate will become "meradimate," the official name for octyl methoxycinnamate will become "octinoxate," the official name for octyl salicylate will become "octisalate" and the official name for phenylbenzimidazole sulfonic acid will become "ensulizole."

Title 21, in Section 352.3, defines the term "Sun Protection Factor," typically abbreviated as "SPF," which is determined by testing unprotected and sunscreen-protected skin using standardized intensities and amounts of ultraviolet radiation. Protected skin for this testing has been treated by an application of a sunscreen product at the rate of 2 mg/cm$^2$, and it is intended that the compositions of this invention will be applied by a user at that same rate to achieve the rated protection levels.

The present invention relates to zinc oxide and avobenzone-containing sunscreen compositions which are stabilized against avobenzone photodegradation by the inclusion of phenylbenzimidazole sulfonic acid. The avobenzone generally will be present in concentrations about 1 to about 3 percent by weight. The zinc oxide generally will be present in concentrations about 1 to about 25 percent by weight, more preferably about 5 to about 15 percent by weight. Useful concentrations of the phenylbenzimidazole sulfonic acid for providing photostability range from about 0.5 to about 4 weight percent, more preferably about 1 to about 3 weight percent. The specific amount of phenylbenzimidazole sulfonic acid that is required to be present in a particular composition to achieve acceptable photostability will depend upon the concentration of avobenzone and, possibly, also on the concentration of zinc oxide; those skilled in the art will be able to easily conduct testing for determining appropriate amounts for their purposes, such as by the method described in the example, infra.

As will be shown, the photostability enhancement of avobenzone by phenylbenzimidazole sulfonic acid is greater at higher zinc oxide concentrations, so zinc oxide concentrations at least about 6 weight percent and up to about 25 weight percent are preferred for compositions of the invention.

Useful sunscreen compositions according to the present invention can be prepared in the form of fluid suspensions, gels, sticks and others, utilizing formulation parameters known in the art. However, the compositions of the invention are more typically emulsions, such as lotions and creams. In many instances it will be preferred to prepare emulsions of the oil-in-water type, since these can appear to the skin as being aqueous in character and therefore give a more pleasant sensation while they are being applied. However, the water-in-oil type of emulsion is also useful since, after application, contained water evaporates; both types of emulsions will leave a nonaqueous residue on the skin.

Emulsion compositions of the invention are required to contain, in addition to the active sunscreening agents, water and at least one emulsifier. One or more other types of components will frequently also be present, such as, without limitation, emulsion builders, emollients, humectants, dry-feel modifiers, waterproofing agents, antimicrobial preservatives, antioxidants, chelating agents, fragrances, colorants and insect repellents.

Emulsions/Emulsifiers

A stable emulsion is a mixture of two immiscible liquids, i.e. liquids that are not mutually soluble, but in the presence of an emulsifier, are mechanically agitated and shaken so thoroughly together that one liquid forms drops in the other one, giving the mixture the appearance of a homogeneous liquid. Liquids can include materials which are solid or solid-like at room temperature, but will liquify at a higher temperature during processing. The presence of an emulsifier enables one of the immiscible liquids to remain in a continuous form, while allowing the other immiscible liquid to remain in a dispersed droplet form. Thus, one function of an emulsifier, a stabilizing compound, is to assist in the production of a stable emulsion. A secondary function of emulsifiers is to provide a thickening or "bodying" to an emulsion. Typically, emulsifiers are molecules with non-polar and polar parts that are able to reside at the interface of the two immiscible liquids. As used herein in reference to the water-in-oil emulsifiers, the term "HLB value" means the hydrophilic/lipophilic balance. The HLB value has been used by those skilled in the emulsion art for selecting emulsifiers useful to prepare, inter alia, water-in-oil emulsions. See U.S. Pat. No. 4,177,259 and references cited therein.

An oil-in-water (o/w) emulsion is a mixture where "oil," or water-insoluble liquid, droplets (the discontinuous phase) are dispersed in a continuous aqueous phase. A water-in-oil (w/o) emulsion is a mixture where aqueous phase droplets (the discontinuous phase) are dispersed in "oil" (a continuous water-insoluble phase). Preferably the composition of the present invention is an oil-in-water emulsion where the oil-soluble actives are combined to form the oil phase, prior to mixture with the water phase. The type of emulsion formed, oil-in-water (o/w) or water-in-oil (w/o), is sometimes determined by the volume ratio of the two liquids provided the ratio is sufficiently high. For example, with 5% water and 95% oil (an o/w phase ratio of 19), the emulsion likely will become w/o. For moderate phase ratios (generally <3), the type of emulsion is decided by several factors, such as order of addition or type of emulsifier. One liquid slowly added to a second liquid with agitation usually results in the second liquid being the continuous phase. Another factor is preferred solubility of the emulsifier, as the phase in which the emulsifier is more soluble will likely be continuous.

More complex emulsions such as double emulsions are formed where an emulsion is dispersed in a continuous phase. For example, in an oil in-water-in oil (o/w/o) emulsion, the water in a continuous water phase containing dispersed oil droplets, is itself dispersed in a continuous oil phase. Similarly, in a water-in oil-in water (w/o/w) emulsion, the oil in a continuous phase containing dispersed water droplets, is itself dispersed in a continuous water phase. These more complex emulsions find use as a system for slow delivery, extraction, etc.

Typical suitable emulsifiers having an HLB value about 1 to about 7 include sorbitan monooleate, sorbitan sesquioleate, sorbitan isostearate, sorbitan trioleate, PEG-22/dodecyl glycol copolymer, PEG-45/dodecyl glycol copolymer, polyglyceryl-3-diisostearate, polyglycerol esters of oleic/isostearic acid, polyglyceryl-6 hexaricinolate, polyglyceryl-4 oleate, polyglyceryl-4 oleate/PEG-8 propylene glycol cocoate, oleamide DEA, sodium glyceryl oleate phosphate and hydrogenated vegetable glycerides phosphate.

Other emulsifiers useful in the present invention may be non-ionic, liquid or solid at room temperature and preferably compatible, i.e., soluble and stable with emollients. Preferred emulsifiers have a HLB value of less than about 5, e.g., sorbitan sequioleate (HLB value is 3.7), sorbitan monooleate (HLB value is 4.3) and sorbitan trioleate (HLB value is 1.8). Other preferred emulsifiers include polymeric emulsifiers such as copolymers of $C_{10}$–$C_{30}$ alkyl acrylates and one or more monomers of acrylic acid or methacrylic acid, also known as Pemulen® TR1 and TR2, trademark of B. F. Goodrich Inc., Cincinnati, Ohio U.S.A. Other emulsifiers include sorbitan esters such as sorbitan isostearate available as Crill 6, trademark of Croda Inc. of New York, N.Y. U.S.A.; polyglyceryl-3 distearate available as Cremophor, trademark of BASF, Parsippany N.J. U.S.A.; and carbomer, which is a homopolymer of acrylic acid crosslinked with an allyl ether of sucrose, available as Carbopol 941, trademark of B. F. Goodrich, Cleveland, Ohio U.S.A.; surfactants such as such as DEA-cetyl phosphate, also known as Amphisol®, trademark of Bernel Chemical Co., Englewood, N.J. U.S.A.; mixtures of arachidyl alcohol, behenyl alcohol and arachidyl glucoside, such as is sold by Seppic Inc. of Fairfield, N.J. U.S.A. using the trademark Montanov 202; and mixtures of cetearyl glucoside and cetearyl alcohol, such as is sold by Cognis Corporation of Cincinnatti, Ohio U.S.A. using the trademark Emulgade PL 68/50.

The foregoing emulsifying agents are mentioned only by way of example. Many other compounds and mixtures are useful, as will be readily appreciated by those skilled in the art.

During preparation of the emulsion, an acid or a base may be added to adjust the pH of one or more ingredients, e.g. to adjust the viscosity of a polymeric thickener, prior to its inclusion in the sunscreen composition. For example, triethanolamine, a base, can be used to increase the pH of the water phase and consequently, modify the desired viscosity of the emulsion. The sunscreen can have a pH of about 6.5 to about 8, preferably from about 6.5 to about 7.5, more preferably the pH of the sunscreen is neutral, i.e. about 7.0. When present together in a composition, certain ingredients such as triethanolamine and stearic acid can form an emulsifier. As is well known, inorganic salts such as sodium chloride also are frequently included in emulsion compositions to obtain desired product stability and other physical properties.

Conveniently, one or more emulsifiers can be used in the compositions of the present invention in amounts ranging from about 0.05 to about 20 weight percent of the emulsion, preferably from about 0.1 to about 15%, more preferably from about 5 to about 10%.

Water

Water is employed in amounts effective to form the emulsion. For hydrophilic or water-loving ingredients, the amount of water should be sufficient to at least solubilize these ingredients. For hydrophobic or water-repelling ingredients, the water should be employed in amounts to serve as the continuous phase of an oil-in water emulsion. Thus, amount of water in the emulsion or composition can range from about 2 to 95 weight %, preferably from 50 to 85%. It frequently is desirable to use purified water, to enhance the predictability of product characteristics.

Emollients

An emollient is an oleaginous or oily substance which helps to smooth and soften the skin, and may also reduce its roughness, cracking or irritation. Typical suitable emollients include mineral, oil, having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil.

Other suitable emollients include squalane, castor oil, polybutene, odorless mineral spirits, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate which is commercially available as Lexol EHP, tradename of Inolex Co. of Philadelphia, Pa. U.S.A., isopropyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glycerol, ricinoleates of alcohols and polyalcohols such as those of isopropyl adipate, hexyl laurate and octyl dodecanoate.

Other suitable emollients which are solids or semi-solids at ambient temperatures may be used in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the sunscreen emulsion in an amount ranging from about 10 to about 50 weight %, preferably about 20 to about 40%.

Humectants

A humectant is a moistening agent that promotes retention of water due to its hygroscopic properties. Suitable humectants include urea, glycerin, polymeric glycols such as poyethylene glycol and polypropylene glycol, and sorbitols. One or more humectants can optionally be included in the in the sunscreen in amounts from about 1 to 10 weight %.

Dry-Feel Modifiers

A dry-feel modifier is an agent which, when incorporated in an emulsion, imparts a "dry feel" to the skin when the emulsion dries. Dry-feel modifiers may also reduce sunscreen migration on the skin. Dry feel modifiers can include starches, talc, kaolin, chalk, zinc oxide, silicone fluids, inorganic salts such as barium sulfate and sodium chloride, $C_6$ to $C_{12}$ alcohols such as octanol; sulfonated oils; surface treated silica, precipitated silica, fumed silica such as Aerosil® available from the Degussa Inc. of New York, N.Y. U.S.A. or mixtures thereof; dimethicone, a mixture of mixture of methylated linear siloxane polymers, available as DC200 fluid, tradename of Dow Corning, Midland, Mich. U.S.A. One or more dry-feel modifiers can optionally be included in the sunscreen in amounts ranging from 0.01 to about 20 weight %, more preferably from about 0.5 to about 6 weight %.

Waterproofing Agents

A waterproofing agent is a hydrophobic material that imparts film forming and waterproofing characteristics to an emulsion. Typical suitable waterproofing agents include copolymers derived from polymerization of octadecene-1 and maleic anhydride in accordance with the published procedures such as those in U.S. Pat. No. 3,860,700 and Reissue No. 28,475. A preferred waterproofing agent is a polyanhydride resin, also known as PA-18, tradename of the Chevron Chemicals Co., San Francisco, Calif. U.S.A. Another preferred waterproofing agent is a copolymer of vinyl pyrollidone and eicosene monomers such as Ganex Polymer, tradename of ISP Inc. of Wayne, N.J. U.S.A.

By the term "waterproofing effective amount of at least one waterproofing agent" means the waterproofing agent(s) is used in amounts effective to allow the sunscreen to remain on the skin after exposure to circulating water for at least 80 minutes using the procedures described in "Sunscreen Drug Products for OTC Human Use", Federal Register, Vol. 43, Aug. 25, 1978, Part 2, pp 38206-38269. One or more waterproofing agents can optionally be included in the sunscreen composition in an amount ranging from about 0.01 to about 10.0 weight percent, preferably about 1.0 to about 10.0 percent.

Antimicrobial Preservatives

An antimicrobial preservative is a substance or preparation which destroys, prevents or inhibits the multiplication/growth of microorganisms in the sunscreen composition and may offer protection from oxidation. Preservatives are used to make self-sterilizing, aqueous based products such as emulsions. This is done to prevent the development of microorganisms that may be in the product during manufacturing and distribution, and during use by consumers who may inadvertently contaminate the products. Typical preservatives include the lower alkyl esters of para-hydroxybenzoates (parabens) especially, methylparaben, propylparaben, isobutylparaben and mixtures thereof, benzyl alcohol and benzoic acid. One or more antimicrobial preservatives can optionally be included in the sunscreen composition in an amount ranging from about 0.001 to about 10 weight percent, more preferably about 0.05 to about 2 percent.

Antioxidants

An antioxidant is a natural or synthetic substance added to the sunscreen to protect from or delay its deterioration due to the action of oxygen from the air, or to protect the skin against damage from free radicals that form due to the action of ultraviolet radiation. Typical suitable antioxidants include propyl, octyl and dodecyl esters of gallic acid, butylated hydroxyanisole (BHA) which is usually as a mixture of ortho and meta isomers, butylated hydroxytoluene (BHT), nordihydroguaiaretic acid, vitamin E, vitamin E acetate, vitamin C and alkylated parabens such as methylparaben and propylparaben. One or more antioxidants can optionally be included in the sunscreen composition in an amount ranging from about 0.001 to about 5 weight percent, preferably about 0.05 to about 2 percent.

Chelating Agents

Chelating agents are substances used to complex or bind metallic ions in a frequently heterocylic ring structure so that the ion is held by chemical bonds from members of the ring. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the sunscreen in amounts ranging from about 0.001 to about 0.1 weight percent.

Fragrances

Fragrances are aromatic compounds which can impart an aesthetically pleasing aroma to the sunscreen composition. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. One or more fragrances can optionally be included in the sunscreen composition in an amount ranging from about 0.001 to about 10 weight percent, preferably about 0.05 to about 5 percent.

Insect Repellents

It frequently is desirable to provide protection against biting and stinging insects, since sunscreens are used in outdoor environments. Useful insect repelling ingredients include synthetic agents such as N.N-diethyl-m-toluamide, also commonly known as "DEET," and natural plant extracts such as citronella, geraniol and others.

Dispensers

The sunscreen emulsions of the present invention can be stored or dispensed in any container suitable for convenient delivery, for example pouring or spraying. Such containers can include, but are not limited to, jars and bottles which permit pouring of the contents, bottles having lotion pumps, pump spray bottles and pressurized aerosol canisters.

Certain aspects of the invention will be further described in the following example, which is not intended to limit the scope of the invention as defined by the appended claims.

EXAMPLE

Comparative photoprotective lotion "A" is prepared using the following ingredients:

| Component | Wt. Percent |
| --- | --- |
| Sodium cetearyl sulfate | 0.5 |
| *PEG-30 dipolyhydroxystearate | 0.3 |
| *Cetearyl glucoside | 1 |
| *Cetearyl alcohol | 1 |
| *Octyl palmitate | 5 |
| *Avobenzone | 2 |
| *Octyl salicylate | 5 |
| *Octocrylene | 1.5 |
| *Homosalate | 12 |

-continued

| Component | Wt. Percent |
|---|---|
| *Isopropyl laurate | 5 |
| *Propyl paraben | 0.1 |
| Benzyl alcohol | 1 |
| Xanthan gum | 0.35 |
| Magnesium aluminum silicate | 1 |
| Disodium EDTA | 0.01 |
| Methyl paraben | 0.2 |
| Polyethylene glycol 400 | 4 |
| Water | q.s. to total 100% |

Modifications of this lotion are prepared to additionally include 3, 6 and 10 wt. percent of a hydrophobic silicone-coated zinc oxide, which is the commercial product sold using the trademark Z-COTE HP1 by BASF Corporation of Mount Olive, N.J. U.S.A. These modified lotions are identified below, respectively, as "A1," "A2" and "A3."

According to an aspect of the present invention, photoprotective lotion "B" is prepared using the following ingredients:

| Component | Wt. Percent |
|---|---|
| Sodium cetearyl sulfate | 0.5 |
| *PEG-30 dipolyhydroxystearate | 0.3 |
| *Cetearyl glucoside | 1 |
| *Cetearyl alcohol | 1 |
| *Octyl palmitate | 8.5 |
| *Avobenzone | 2 |
| *Octyl salicylate | 5 |
| *Octocrylene | 1.5 |
| *Homosalate | 5 |
| *Isopropyl laurate | 8.5 |
| *Propyl paraben | 0.1 |
| Benzyl alcohol | 1 |
| Xanthan gum | 0.35 |
| Magnesium aluminum silicate | 1 |
| Disodium EDTA | 0.01 |
| Methyl paraben | 0.2 |
| Polyethylene glycol 400 | 4 |
| Triethanolamine | 0.8 |
| Phenylbenzimidazole sulfonic acid | 1 |
| Water | q.s. to total 100% |

Modifications of this base lotion are prepared to additionally include 3, 6 and 10 wt. percent of the above-identified Z-COTE HP1 zinc oxide. These modified lotions are identified below, respectively, as "B1," "B2" and "B3."

All lotions are prepared using the following procedure:

(1) the ingredients identified above with an asterisk are combined with mixing and heated to about 65° C. then, after a homogenous mixture is obtained, the zinc oxide (if required) is added;

(2) the water, disodium EDTA, polyethylene glycol, triethanolamine (if required) and phenylbenzimidazole sulfonic acid (if required) are combined and mixed to obtain homogeneity, magnesium aluminum silicate and xanthan gum are added and the combination is mixed and heated to about 65° C., then the methylparaben and sodium cetearyl sulfate are added;

(3) the heated combination of (1) is added to the heated combination of (2), with continuous mixing to form an emulsion, and the emulsion is homogenized by passing through a commercial homogenizer for 5 minutes;

(4) under continuous mixing, the emulsion is allowed to cool to less than about 40° C., then the benzyl alcohol is added and the mixture continues to cool to room temperature; and (5) additional water is added, with mixing, as needed to compensate for evaporative losses occurring during the procedure.

The various lotions have the following properties:

| Lotion | SPF Value | Lotion pH |
|---|---|---|
| A | 23.3 | 5.41 |
| A1 | 24.3 | |
| A2 | 36.7 | |
| A3 | 42.9 | 7.11 |
| B | 26.5 | |
| B1 | 27.5 | |
| B2 | 38.9 | |
| B3 | 44 | 7.57 |

The lotions are tested to determine photostability by weighing up to 20 milligram portions (the target being 15 milligrams) of each lotion onto glass microscope slides having a surface area of 12.5 cm$^2$ and spreading the lotion evenly over the upper surface of the slides. Samples are allowed to air-dry in the dark for at least 30 minutes and then are placed on a rotating turntable and irradiated using a WG 320 filtered 1000-watt xenon arc solar simulator (Kratos Analytical, Model LH-153, currently being sold by Spectral Energy Corp., Westwood, N.J. U.S.A.) delivering 30 joules of energy over a period of about 60 minutes.

The avobenzone content of irradiated lotion samples, selected to have had 13–17 milligrams of lotion applied to a slide, and non-irradiated control lotions (having similar amounts spread onto slides and dried as described above) is analyzed by ultraviolet absorption spectrophotometry at a wavelength of 360 nanometers. Each slide is placed into 50 milliliters of isopropanol in a glass jar, the dried sunscreen coating is disrupted from the slide by rubbing with a rubber finger cot-covered finger, the jar is closed and vigorously shaken to solubilize the sunscreen active ingredients and then samples of the alcohol solution are analyzed in the spectrophotometer. Absorbance values for samples are compared to curves obtained from isopropanol solutions of standard sunscreen preparations that contain known amounts of avobenzone. The following results are obtained:

| Lotion | % of original Avobenzone before exposure | % of original Avobenzone after exposure |
|---|---|---|
| A | 100.8 ± 1.0 | 81.5 ± 6.6 |
| A1 | 99.0 ± 0.5 | 76.8 ± 0.9 |
| A2 | 96.6 ± 7.5 | 72.9 ± 1.1 |
| A3 | 101.6 ± 3.3 | 66.8 ± 4.3 |
| B | 98.6 ± 1.6 | 89.1 ± 2.7 |
| B1 | 97.8 ± 1.6 | 89.2 ± 3.8 |
| B2 | 100.9 ± 0.6 | 91.1 ± 1.7 |
| B3 | 101.0 ± 3.2 | 87.2 ± 5.2 |

These results show that avobenzone photostability is enhanced when phenylbenzimidazole sulfonic acid is present in sunscreen compositions. Zinc oxide does not adequately protect avobenzone against photodegradation, and photostability is improved by also including phenylbenzimidazole sulfonic acid in the composition.

What is claimed is:

1. A sunscreen composition comprising avobenzone, zinc oxide in an amount from about 6 to about 25 weight percent and sufficient phenylbenzimidazole sulfonic acid to stabilize the avobenzone against photodegradation, wherein the composition does not contain a diester or polyester of a naphthalene dicarboxylic acid.

2. The composition of claim 1, wherein the concentration of avobenzone is about 1 to about 3 weight percent, and the concentration of phenylbenzimidazole sulfonic acid is about 0.5 to about 4 weight percent.

3. A method for protecting the skin against ultraviolet radiation, comprising applying to the skin an effective amount of the composition of claim 1.

4. A method for protecting the skin against ultraviolet radiation, comprising applying to the skin an effective amount of the composition of claim 2.

5. The composition of claim 1, wherein the concentration of zinc oxide is about 10 weight percent.

6. The composition of claim 1, wherein the concentration of phenylbenzimidazole sulfonic acid is about 1 weight percent.

7. The composition of claim 1, which is in the form of an emulsion.

8. The composition of claim 7, wherein the emulsion is an oil-in-water emulsion.

9. A method for increasing the SPE value of a sunscreen composition comprising avobenzone and zinc oxide, wherein zinc oxide is present in the composition in an amount of about 6 to about 25 weight percent, the method comprising adding to the composition an amount of phenylbenzimidazole sulfonic acid sufficient to photostabilize avobenzone, thereby increasing the SPF value, wherein the composition does not contain a diester or polyester of a naphthalene dicarboxylic acid.

10. The method of claim 9 wherein zinc oxide is present in the composition in an amount of about 10 weight percent.

11. The method of claim 9 wherein the amount of phenylbenzimidazole sulfonic acid is about 1 weight percent.

12. A method for improving the photostability of avobenzone in a composition comprising avobenzone and zinc oxide, wherein zinc oxide is present in the composition in an amount of about 6 to about 25 weight percent, the method comprising adding to the composition an amount of phenylbenzimidazole sulfonic acid sufficient to photostabilize avobenzone, wherein the composition does not contain a diester or polyester of a naplithalene dicarboxylic acid.

13. The method of claim 10 wherein zinc oxide is present in the composition in an amount of about 10 weight percent.

14. The method of claim 10 wherein the amount of phenylbenzimidazole sulfonic acid is about 1 weight percent.

* * * * *

UNITED STATES PATENT AND TRADEMARK OFFICE
CERTIFICATE OF CORRECTION

PATENT NO.        : 7,244,416 B2
APPLICATION NO.   : 10/645253
DATED             : July 17, 2007
INVENTOR(S)       : Thomas A. Meyer It is certified that error appears in the above-identified patent and that said Letters Patent is hereby corrected as shown below:

In the Claims:

Claim 9, Col. 11, Line 27:   Please correct "SPE" to -- SPF --

Signed and Sealed this

Sixth Day of November, 2007

JON W. DUDAS
*Director of the United States Patent and Trademark Office*